(12) United States Patent
Boons et al.

(10) Patent No.: US 7,105,710 B2
(45) Date of Patent: Sep. 12, 2006

(54) PROCESS OF PREPARING AN ALKYLENE GLYCOL

(75) Inventors: Petrus Johannes Geradus Boons, Fort Sasketchewan (CA); Eugene Marie Godfried Andre Van Kruchten, Amsterdam (NL); Dominicus Maria Rekers, Amsterdam (NL); Mathias Jozef Paul Slapak, Moerdijk (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/948,867

(22) Filed: Sep. 24, 2004

(65) Prior Publication Data
US 2005/0119510 A1  Jun. 2, 2005

(30) Foreign Application Priority Data
Sep. 26, 2003 (EP) ................... 03256074

(51) Int. Cl.
*C07C 29/00* (2006.01)
(52) U.S. Cl. ...................................... 568/867
(58) Field of Classification Search ................. 568/867
See application file for complete search history.

(56) References Cited
U.S. PATENT DOCUMENTS
4,701,571 A * 10/1987 Soo et al. ................... 568/867
6,124,508 A    9/2000 Van Kruchten ............. 568/867
6,160,187 A *  12/2000 Strickler et al. ............ 568/867

FOREIGN PATENT DOCUMENTS
| EP | 0160330 | 11/1990 |
| EP | 741683 | 10/1998 |
| WO | 95/20559 | 8/1995 |
| WO | 99/31034 | 6/1999 |
| WO | 02/26675 | 4/2002 |

\* cited by examiner

*Primary Examiner*—Samuel Barts
*Assistant Examiner*—Kellette Gale

(57) ABSTRACT

A process of preparing an alkylene glycol which process involves: i) reacting a respective alkylene oxide and water in a first reactor, ii) removing from the first reactor a reactor output mixture comprising an alkylene glycol and unreacted water, iii) transferring a proportion of the reactor output mixture to a distillation unit and a proportion of the reaction output mixture to a second reactor containing a catalyst, iv) reacting the reaction output mixture in the second reactor with a further amount of the respective alkylene oxide, and v) transferring a reactor output mixture from the second reactor to a distillation unit.

21 Claims, 1 Drawing Sheet

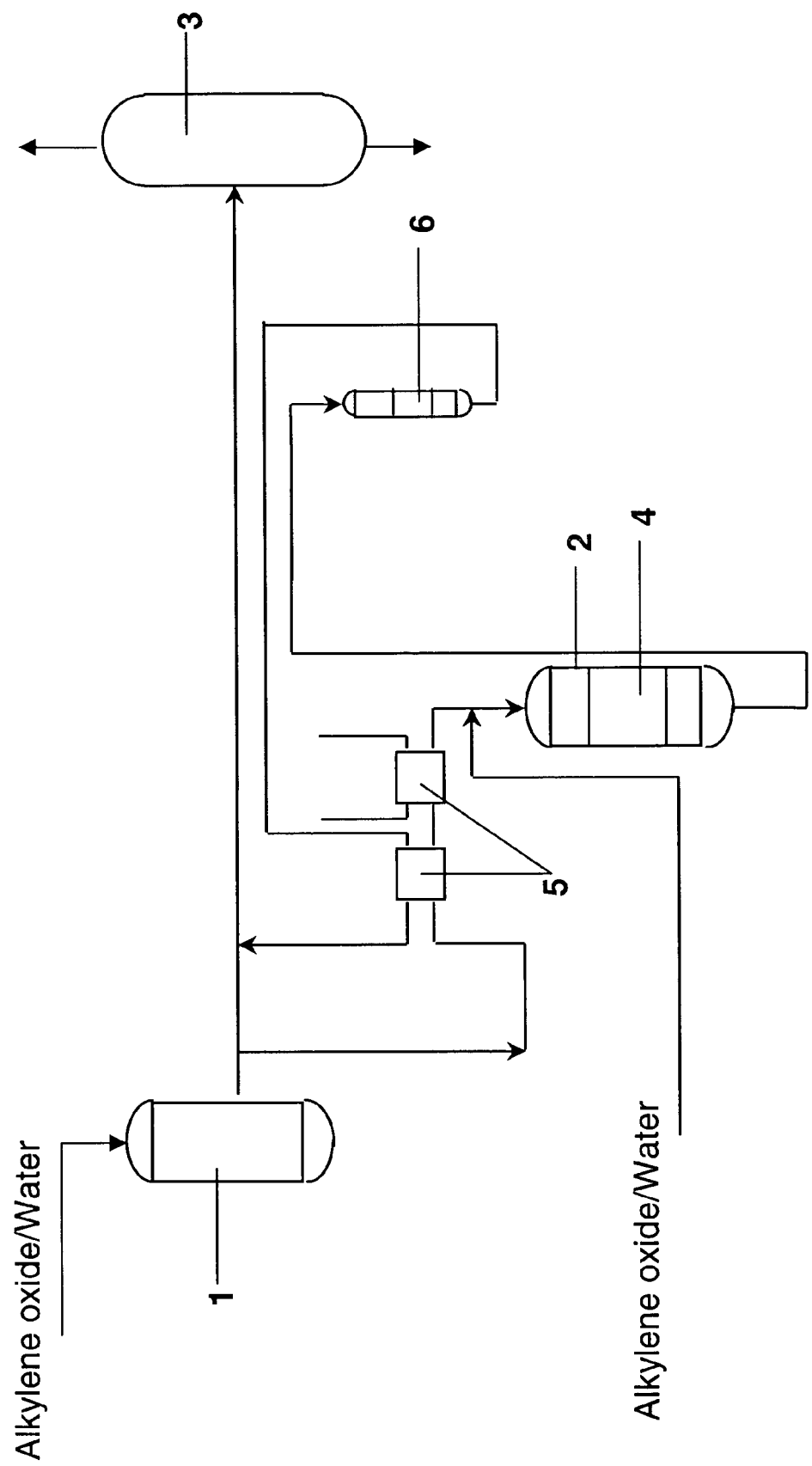
Figure

PROCESS OF PREPARING AN ALKYLENE GLYCOL

The present invention relates to a process of preparing an alkylene glycol.

BACKGROUND OF THE INVENTION

Alkylene glycols, in particular monoalkylene glycols, are of established commercial interest. For example, monoalkylene glycols are being used in anti-freeze compositions, as solvents and as base materials in the production of polyalkylene terephthalates e.g. for fibers and bottles.

The production of alkylene glycols by liquid phase hydrolysis of alkylene oxides is known. In commercial production the hydrolysis is performed without a catalyst by adding a large excess of water, e.g. 15 to 30 moles of water per mole of alkylene oxide. The reaction is considered to be a nucleophilic substitution reaction, whereby opening of the alkylene oxide ring occurs, water acting as the nucleophile. Because the primarily formed monoalkylene glycol also acts as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product. Removing this additional water increases production costs as it is energy intensive and requires large-scale distillation facilities.

The demand for monoalkylene glycols has risen significantly in recent years and further growth is expected on account of the increasing popularity of monoalkylene glycol derived products. Most existing commercial alkylene glycol production facilities already operate at or close to maximum (design) capacity. Therefore, to meet the increased demand more efficient methods of producing monoalkylene glycols are required.

In commercial thermal alkylene glycols production processes, the limiting factor on the amount of monoalkylene glycol production is frequently the distillation of water from the aqueous glycol reactor product, as removing the large amounts of water required for high selectivity is a relatively lengthy process. This is problematic as the distillation step acts as a bottleneck, restricting the overall amount of production.

One method of overcoming this problem would be to reduce the ratio of water to alkylene oxide employed in the process. However, this would also increase the relative yield of less desirable higher alkylene glycol products, and possibly necessitate an expansion of facilities to remove and purify the higher alkylene glycol products from the monoalkylene glycol product.

Due to the size and cost of distillation and purification apparatus required to remove water and/or higher glycols, increasing distillation capacity is in many cases neither a practical nor cost-effective solution. Accordingly, it would be advantageous if there was a flexible means with which to overcome this problem such that glycol production could be increased while retaining high selectivity to monoalkylene glycol products.

Catalytic processes for converting alkylene oxides to alkylene glycols have been investigated and catalysts capable of promoting a higher selectivity to monoalkylene glycol product at reduced water levels are known, (e.g. EP-A 015649, EP-A 0160330, WO 95/20559 and U.S. Pat. No. 6,124,508). For some catalysts, such as the quaternary phosphonium cation-containing catalysts of U.S. Pat. No. 6,124,508, it is mentioned that in order to save the catalyst it may be advantageous to subject the alkylene oxide feed stream to partial thermal hydrolysis before completing the hydrolysis catalytically.

SUMMARY OF THE INVENTION

The present invention is directed to a previously unconsidered use of a catalytic method of glycol production that enables production amounts to be increased while maintaining high selectivity to monoalkylene glycol product. Accordingly, the present invention is directed to a process of preparing an alkylene glycol which process comprises:—
 i) reacting a respective alkylene oxide and water in a first reactor,
 ii) removing from the first reactor a reactor output mixture comprising an alkylene glycol and unreacted water,
 iii) transferring a proportion of the reactor output mixture to a distillation unit and a proportion of the reaction output mixture to a second reactor comprising a catalyst,
 iv) reacting the reaction output mixture in the second reactor with a further amount of the respective alkylene oxide, and
 v) transferring a reactor output mixture from the second reactor to a distillation unit.

BRIEF DESCRIPTION OF THE DRAWING

The FIGURE is a schematic depiction of a preferred embodiment of the present invention.

DETAILED DESCRIPTION OF THE INVENTION

The present invention makes use of a catalyst in the second reactor to allow a further amount of alkylene oxide to be converted to alkylene glycol by reaction with water already present in the output mixture from the first reactor. In this way, overall yields of product may be increased with relatively little or no increase in the total amount of water employed in the process. This is possible as the catalytic reaction has a higher selectivity to monoalkylene glycol product at the same or a lower ratio of water to ethylene oxide than the thermal reaction.

Catalysts that may be employed in the present process are known in the art. Preferred catalysts are those comprising an ion exchange resin as a solid support, in particular the strongly basic (anionic) Ion exchange resin wherein the basic groups are quaternary ammonium or quaternary phosphonium. The ion exchange resins may be based on vinylpyridine, polysiloxanes, as well as other solid supports having electropositive complexing sites of an inorganic nature, such as carbon, silica, silica-alumina, zeolites, glass and clays such as hydrotalcite. Further, immobilized complexing macrocycles such as crown ethers, etc. can be used as well as a solid support.

Preferably, the catalyst is based on a strongly basic quaternary ammonium resin or a quaternary phosphonium resin. The catalyst is most preferably based on an anion exchange resin comprising a trimethylbenzyl ammonium group. Examples of commercially available anion exchange resins on which the catalyst of the present invention may be based include LEWATIT M 500 WS (LEWATIT is a trademark), DUOLITE A 368 (DUOLITE is a trademark) and AMBERJET 4200 (AMBERJET is a trademark), DOWEX MSA-1 (DOWEX is a trademark), MARATHON-A and MARATHON-MSA (MARATHON is a trademark) (all based on polystyrene resins, cross-linked with divinyl benzene) and Reillex HPQ (based on a polyvinylpyridine resin, cross-linked with divinyl benzene).

The anion exchange resin in the fixed bed of solid catalyst may comprise more than one anion. Preferably, the anion is selected from the group of bicarbonate, bisulfite, metalate and carboxylate anions.

When the anion is a carboxylate anion, it is preferred that the anion is a polycarboxylic acid anion having in its chain molecule one or more carboxyl groups and one or more carboxylate groups, the individual carboxyl and/or carboxylate groups being separated from each other in the chain molecule by a separating group consisting of at least one atom. Preferably the polycarboxylic acid anion is a citric acid derivative, more preferably a mono-anion of citric acid.

Most preferably the anion is a bicarbonate anion.

A solid catalyst which has given particularly good results when employed in the process of the present invention, is a catalyst based on a quaternary ammonium resin, preferably a resin comprising a trimethylbenzyl ammonium group, and wherein the anion is a bicarbonate anion.

The alkylene oxides used as starting materials in the process of the present invention, have their conventional definition, i.e. they are compounds having a vicinal oxide (epoxy) group in their molecules.

Preferred alkylene oxides are alkylene oxides of the general formula:—

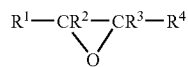

wherein each of $R^1$ to $R^4$ independently represents a hydrogen atom or an optionally substituted alkyl group having from 1 to 6 carbon atoms. Any alkyl group, represented by $R^1$, $R^2$, $R^3$ and/or $R^4$, preferably has from 1 to 3 carbon atoms. Optional substituents on the alkyl groups include hydroxyl groups. Preferably, $R^1$, $R^2$, and $R^3$ represent hydrogen atoms and $R^4$ represents a non-substituted $C_1$–$C_3$-alkyl group and, more preferably, $R^1$, $R^2$, $R^3$ and $R^4$ all represent hydrogen atoms.

Examples of alkylene oxides which may conveniently be employed include ethylene oxide, propylene oxide, 1,2-epoxybutane, 2,3-epoxybutane and glycidol. The alkylene oxide is preferably ethylene oxide or propylene oxide; ethylene glycol and propylene glycol being alkylene glycols of particular commercial importance. Most preferably the alkylene oxide of the present invention is ethylene oxide or propylene oxide and the alkylene glycol is ethylene glycol or propylene glycol.

The first reactor of the present invention may conveniently be a conventional thermal reactor as is widely used for the hydrolysis of alkylene oxides to alkylene glycols, and the reaction conditions in the first reactor will generally be in accordance with those commonly used in thermal alkylene glycol production, e.g. a water/alkylene oxide ratio of 15 to 30 moles of water per mole of alkylene oxide, a temperature in the range of from 150 to 250° C., and a pressure in the range of from 500 to 5000 kPa. The first reactor may comprise a single thermal reactor or two or more thermal reactors arranged in either a parallel or series configuration.

It is an advantageous feature of the present invention that by varying the amount of first reactor output mixture directed to the second reactor it is possible to vary the output of mono-, di- and trialkylene glycol product produced to suit demand. For example, when a higher proportion of monoalkylene glycol product is required, the proportion of first reactor output mixture routed to the second reactor may conveniently be increased. Conversely, if it is desired to produce a larger quantity of di- or trialkylene glycol, the amount of output mixture fed to the second reactor may be adjusted appropriately. As will be understood by those skilled in the art, the present process may further comprise suitable detection and adjusting means to allow the proportion of reaction output mixture fed to the second reactor to be optimized to attain the required product ratios.

In general, the proportion of reaction output mixture from the first reactor transferred to the second reactor is preferably in the range of from 25 to 100% wt of the total amount of first reactor output mixture, more preferably 30 to 99% wt, even more preferably 35 to 70% wt, and most preferably 40 to 60% wt.

The second reactor of the present invention may comprise a single catalyst-containing reactor, or a reactor system comprising two or more catalyst-containing reactors arranged in either a parallel or series configuration. The conditions employed in the second reactor may vary depending on the catalyst employed, the constituents of the reactor output mixture fed to the second reactor, and the desired overall selectivity to mono-, di- and trialkylene glycol product. However, in general, the temperature in the second reactor will conveniently be in the range of from 60 to 150° C., more conveniently 70 to 100° C.; and the pressure conveniently in the range of from 500 to 5000 kPa, more conveniently 500 to 3000 kPa. Moreover, the optimal liquid hourly space velocity of the reactants through the reactor will preferably be in the range of from 0.5 to 15 l/l·h, more preferably 1 to 10 l/l·h.

In certain embodiments of the present invention it may be beneficial to add carbon dioxide to the second (catalytic) reactor. Such carbon dioxide may conveniently be added directly to the reactor or it may be added to the alkylene oxide feed. If carbon dioxide is to be added, the amount of carbon dioxide added may be varied to obtain optimum performance in relation to other reaction parameters, in particular the type of catalyst employed. However the amount added will preferably be less than 0.1% wt, more preferably less than 0.01% wt, based on a total amount of reactants in the second reactor.

When the second reactor comprises a fixed bed reactor, the process of the present invention may be operated in up-flow or down-flow operation. Down-flow operation is preferred. The reactor may be maintained under isothermal, adiabatic or hybrid conditions. Isothermal reactors are generally shell- and tube reactors, mostly of the multitubular type, wherein the tubes contain the catalyst and coolant passes outside the tubes. Adiabatic reactors are not cooled, and the product stream leaving them may be cooled in a separate heat exchanger. Under certain chosen circumstances it may be advantageous to use a recycle reactor in which part of the outlet of the reactor containing the catalyst is recycled back to the inlet of the same reactor. In order to accommodate any swelling of the catalyst during operation, the reactor volume can advantageously be greater than the volume occupied by the catalyst therein, for example 10 to 70 vol % greater.

The present invention provides a highly flexible means of alkylene glycol production. As well as allowing glycol to be produced at a higher rate, the output of mono-, di- and trialkylene glycol product produced may be conveniently adjusted to suit demand. Further, the invention may very conveniently be implemented in existing alkylene glycol production facilities to increase production rates without compromising selectivity.

The invention is now further described with reference to the FIGURE. In the preferred process depicted in the FIGURE, water and alkylene oxide are fed to a first reactor 1 wherein they are reacted at elevated temperature to produce a reactor output mixture comprising alkylene glycol, unreacted water and optionally some unreacted alkylene oxide. The reactor output mixture from the first reactor is then divided into two streams such that a proportion of the mixture is fed to a distillation unit 3, while a proportion is fed, via heat exchangers 5, to a second reactor 2 containing a catalyst bed 4.

In the second reactor 2, the reactor output mixture from the first reactor is reacted with a further amount of alkylene oxide, and optionally water. In the preferred process of FIG. 1, the reaction output mixture from the second reactor 2 is transferred to the distillation unit 3 via a post-reactor 6 and heat exchangers 5.

It is not an essential feature of the present invention that the same distillation unit be employed to remove water from both the reactor output mixture from the first and second reactors. However, in certain applications, in particular where the present process is implemented in an existing glycol production facility to overcome a bottleneck problem, it is preferred that the reactor output mixture from the second reactor is transferred to the same distillation unit to which a proportion of the reactor output mixture from the first reactor is transferred.

The distillation unit may comprise any distillation apparatus known in the art for the removal of water from alkylene glycols. Conveniently, the distillation unit may be a unit already present in an existing glycols production facility, as is particularly advantageous when the present invention is implemented to increase the production capacity of an existing plant. Such distillation units will typically comprise a multiple effect evaporation system with subsequent vacuum distillation. After water removal the monoalkylene glycol product may then be purified in a purification column wherein monoalkylene glycol product is extracted as a side stream, while the bottom stream is sent to further purification columns for isolation of higher alkylene glycol products.

In accordance with the present invention post-reactor(s) 6 may be employed, for example as depicted in the preferred embodiment of FIG. 1, to ensure complete conversion of all starting material alkylene oxide to glycol product and/or to remove any contaminants such as amines or phosphines that may have leached into the reaction output mixture from the catalyst. Where necessary, an effective way of removing such contaminants is to pass the output mixture through a post-reactor comprising a strongly acidic ion exchange resin, for example of an exchange resin of the sulfonic type, e.g. as available under the trade names AMBERLYST 15, AMBERJET 1500H, AMBERJET 1200H, DOWEX MSC-1, DIANON SK1B, LEWATIT VP OC 1812, LEWATIT S 100 MB, LEWATIT S 100 G1.

The process of the present invention may be carried out in batch operation. However, in particular for large scale embodiments it is preferred to operate the process continuously.

The present invention further provides a process of permitting a variable rate of alkylene glycol(s) production from alkylene oxide and water, which process comprises use of a catalytic conversion reactor in combination with a thermal conversion reactor. A thermal conversion reactor is a reactor wherein the reaction may be promoted by heat alone and does not contain a catalyst. A catalytic conversion reactor is a reactor comprising a catalyst capable of promoting the conversion of alkylene oxide to alkylene glycol(s). By variable rate of alkylene glycol(s) production it is meant that the overall amount of monoalkylene glycol produced may be increased as compared with the use of a thermal reactor alone without any loss in selectivity. In said process, the thermal and catalytic conversion reactors may be positioned in either a series or parallel configuration. Preferably the reactors are in a series configuration, more preferably with the catalytic conversion reactor positioned down stream of the thermal conversion reactor.

The present invention will be further understood from the following illustrative example.

EXAMPLE 1

A feed composition corresponding to the reactor output from a thermal reactor was reacted with a further amount of ethylene oxide in the presence of a catalyst in an adiabatic reactor.

The catalyst employed in Example 1 comprised a quaternary ammonium resin and a bicarbonate anion. The catalyst was prepared by washing an ion exchange resin of the quaternary ammonium type in the chloride form (AMBERJET 4200, ex-Rohm & Hass, exchange capacity 1.3 meq/ml) as follows: I) 150 ml of wet catalyst was slurried in a water filled glass tube, ii) the chloride anion was exchanged by treatment with a sodium-bicarbonate solution (10 times molar excess in 2500 g of water) for approximately 5 hours (Liquid Hourly Space Velocity=4 l/l·h), and iii) the exchanged resin was washed with 1200 ml of water for 2 h (LHSV=4 l/l·h). In the resulting catalyst the chloride anions from the AMBERJET 4200 had been almost completely exchanged with the desired bicarbonate anions, the final chloride content of the catalyst being 32 ppm.

The adiabatic reactor comprised a reactor tube filled with catalyst and fitted inside a stainless steel pipe. The reactor tube had an internal diameter of 20 mm and a length of 24 cm. The reactor tube was insulated with a Teflon layer placed between the tube and the stainless steel pipe. The stainless steel pipe was electrically heated to compensate for heat loss only. In operation the feed was preheated prior to mixing with the additional ethylene oxide to achieve the required inlet temperature.

The feed stream entering the reactor consisted of 17.1% wt monoethylene glycol, 2.1% wt diethylene glycol, 77.9% wt water, 3% wt ethylene oxide and had a carbon dioxide content of 7 ppm. The contents of the above feed stream correspond to the output of a thermal reactor to which an additional amount of ethylene oxide has been added, and were determined on the basis of an input to the thermal reactor of 83% wt water and 14% wt ethylene oxide, a selectivity to monoethylene glycol in the thermal reactor of 87.4%, and the addition of a further amount of 3% wt of ethylene oxide to the output of the thermal reactor, all weights based on the total amount of water and ethylene oxide employed in the process.

The adiabatic reactor was loaded with 42 ml of wet catalyst and the feed was pumped at 1000 kPa pressure into the reactor. The liquid hourly space velocity (LHSV) through the reactor was 4.7 l/l·h, the inlet temperature was from 84–85° C. and the outlet temperature from 91–93° C. The reactor was run continuously and the reactor output periodically analyzed by gas chromatography to determine the conversion of ethylene oxide in the catalytic reactor and the selectivity to monoethylene glycol in the total mixture. The results are shown in Table 1.

TABLE 1

| Run (hour) | [1]EO Conversion in catalytic reactor (%) | [2]Selectivity to MEG in reaction mixture (%) |
|---|---|---|
| 127 | 95.4 | 88.7 |
| 176 | 96.3 | 88.8 |
| 201 | 96.3 | 88.8 |
| 254 | 96.6 | 88.6 |
| 377 | 92.3 | 88.6 |
| 460 | 93.6 | 88.6 |
| 621 | 95.5 | 88.7 |
| 710 | 95.5 | 88.7 |
| 780 | 92.9 | 88.7 |
| 892 | 93.3 | 88.8 |
| 1055 | 96.5 | 88.7 |
| 1151 | 94.4 | 88.6 |
| 1218 | 94.6 | 88.7 |
| 1284 | 96.0 | 89.1 |
| 1373 | 95.6 | 88.9 |
| 1445 | 95.0 | 88.8 |
| 1616 | 93.9 | 88.6 |
| 1704 | 92.8 | 88.8 |
| 1886 | 92.6 | 88.6 |
| 2024 | 91.1 | 88.5 |
| 2190 | 89.3 | 88.5 |
| 2281 | 90.6 | 88.5 |
| 2392 | 87.3 | 88.4 |
| 2554 | 88.4 | 88.4 |
| 2556 | 87.6 | 88.2 |

[1]EO conversion (mol %) = 100 × (MEG + 2DEG + 3TEG + 4TTEG)/(EO + MEG + 2DEG + 3TEG + 4TTEG)
[2]MEG selectivity (mol %) = 100 × (MEG)/(MEG + 2DEG + 3TEG + 4TTEG)

From Table 1 it can be seen that the overall selectivity to monoethylene glycol (MEG) in the total reaction mixture has been improved from 87.4% to in excess of 88% despite the addition and conversion of the extra amount of ethylene oxide (EO). Accordingly, Example 1 demonstrates the capability of a catalytic reactor, when used in accordance with the present invention, to de-bottleneck a thermal monoethylene glycol plant with no loss in overall selectivity.

We claim:

1. A process of preparing an alkylene glycol which process comprises:
   i) reacting a respective alkylene oxide and water in a first reactor;
   ii) removing from the first reactor a reactor output mixture comprising an alkylene glycol and unreacted water;
   iii) transferring a proportion of the reactor output mixture to a distillation unit and a proportion of the reaction output mixture to a second reactor comprising a catalyst;
   iv) reacting the reaction output mixture in the second reactor with a further amount of the respective alkylene oxide; and
   v) transferring a reactor output mixture from the second reactor to a distillation unit.

2. The process of claim 1, in which the proportion of the reactor output mixture from the first reactor transferred to the second reactor is in the range of from 30 to 99 wt % of the total amount of first reactor output mixture.

3. The process of claim 1, in which the catalyst in the second reactor comprises a fixed bed of a solid catalyst based on an anion exchange resin.

4. The process of claim 3, in which the anion exchange resin is a strongly basic quaternary ammonium resin or quaternary phosphonium resin.

5. The process of claim 3, in which the catalyst anion is selected from the group of bicarbonate, carboxylate, bisulphite and metallate anions.

6. The process of claim 1, in which the reactor output mixture from the second reactor is transferred to the same distillation unit to which a proportion of the reactor output mixture from the first reactor is transferred.

7. The process of claim 1, in which the reactor output mixture from the second reactor is further treated in one or more post-reactors before being transferred to the distillation unit.

8. The process of claim 1, in which the alkylene oxide is ethylene oxide or propylene oxide and the alkylene glycol is ethylene glycol or propylene glycol.

9. A process for producing one or more alkylene glycol from alkylene oxide and water, which process comprises:
   producing one or more alkylene glycols in a thermal conversion reactor to produce a thermal conversion reactor output mixture;
   separating the thermal conversion reactor output mixture into a first portion and a second portion; and,
   reacting the first portion with a further amount of alkylene oxide in a catalytic conversion reactor in the presence of catalyst to produce a catalytic conversion reactor output mixture and, transferring the second portion of the thermal conversion reactor output mixture to a distillation unit.

10. The process of claim 9 further comprising transferring the catalytic conversion reactor output mixture to a distillation unit.

11. The process of claim 9 wherein the first portion is from 30 to 99 wt % of the total amount of the thermal conversion reactor output mixture.

12. The process of claim 10 wherein the first portion is from 30 to 99 wt % of the total amount of the thermal conversion output mixture.

13. The process of claim 9 wherein the first portion is from 35 to 70 wt % of the total amount of the thermal conversion output mixture.

14. The process of claim 10 wherein the first portion is from 35 to 70 wt % of the total amount of the thermal conversion reactor output mixture.

15. The process of claim 9, in which
   the alkylene oxide is selected from the group consisting of ethylene oxide and propylene oxide; and,
   the alkylene glycol is selected from the group consisting of ethylene glycol and propylene glycol.

16. The process of claim 10, in which
   the alkylene oxide is selected from the group consisting of ethylene oxide and propylene oxide; and,
   the alkylene glycol is selected from the group consisting of ethylene glycol and propylene glycol.

17. A process for producing one or more alkylene glycol from alkylene oxide and water, which process comprises:
   producing one or more alkylene glycols in a thermal conversion reactor to produce a thermal conversion reactor output mixture;

separating the thermal conversion reactor output mixture into a first portion and a second portion, the first portion being from 40 to 60 wt % of the total amount of first reactor output mixture; and, reacting the first portion with a further amount of alkylene oxide in a catalytic conversion reactor in the presence of catalyst to produce a catalytic conversion reactor output mixture and, transferring the second portion of the thermal conversion reactor output mixture to a distillation unit.

18. The process of claim 17 further comprising transferring catalytic conversion reactor output mixture to a distillation unit.

19. The process of claim 18 in which the catalytic conversion reactor output mixture and the second portion of the thermal conversion reactor output mixture are transferred to the same distillation unit.

20. The process of claim 17, in which
the alkylene oxide is selected from the group consisting of ethylene oxide and propylene oxide; and,
the alkylene glycol is selected from the group consisting of ethylene glycol and propylene glycol.

21. The process of claim 19, in which
the alkylene oxide is selected from the group consisting of ethylene oxide and propylene oxide; and,
the alkylene glycol is selected from the group consisting of ethylene glycol and propylene glycol.

* * * * *